(12) United States Patent
Conder et al.

(10) Patent No.: US 8,962,681 B2
(45) Date of Patent: Feb. 24, 2015

(54) USE OF AMINOACETONITRILE DERIVATIVES AGAINST ENDOPARASITES

(71) Applicant: Zoetis LLC, Florham Park, NJ (US)

(72) Inventors: George Anthony Conder, Kalamazoo, MI (US); Kevin Evans, Florham Park, NJ (US); Patrick F. M. Meeus, Kalamazoo, MI (US); Debra Jean Woods, Kalamazoo, MI (US)

(73) Assignee: Zoetis LLC, Florham Park, NJ (US)

( * ) Notice: Subject to any disclaimer, the term of this patent is extended or adjusted under 35 U.S.C. 154(b) by 0 days.

(21) Appl. No.: 14/351,945

(22) PCT Filed: Oct. 8, 2012

(86) PCT No.: PCT/IB2012/055436
§ 371 (c)(1),
(2) Date: Apr. 15, 2014

(87) PCT Pub. No.: WO2013/057624
PCT Pub. Date: Apr. 25, 2013

(65) Prior Publication Data
US 2014/0243408 A1    Aug. 28, 2014

Related U.S. Application Data

(60) Provisional application No. 61/549,027, filed on Oct. 19, 2011.

(51) Int. Cl.
*A61K 31/277* (2006.01)
*A61K 45/06* (2006.01)
*C07C 381/00* (2006.01)

(52) U.S. Cl.
CPC .............. *A61K 31/277* (2013.01); *C07C 381/00* (2013.01); *A61K 45/06* (2013.01)
USPC .......................................... 514/521; 558/392

(58) Field of Classification Search
CPC .............................. A61K 31/277; A61K 45/06
USPC ........................................... 514/521; 558/392
See application file for complete search history.

(56) References Cited

FOREIGN PATENT DOCUMENTS

| WO | 2005/044784 | 5/2005 |
|----|-------------|--------|
| WO | 2005/058802 | 6/2005 |
| WO | 2008/096231 | 8/2008 |
| WO | 2010/063767 | 6/2010 |

OTHER PUBLICATIONS

PCT International Search Report, PCT/IB2012/055436, mailed Feb. 5, 2013 (5 pages).

*Primary Examiner* — Raymond Henley, III
(74) *Attorney, Agent, or Firm* — Paul M. Misiak

(57) ABSTRACT

The present invention relates to a method of treating a parasitic infection in an animal, particularly a filarial endoparasitic infection, comprising administering an effective amount of a Formula (I) compound or a Formula (II) compound

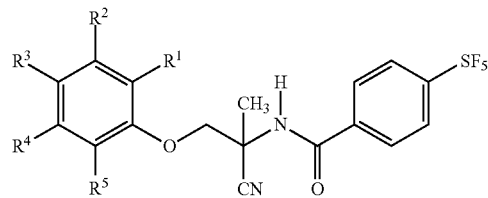

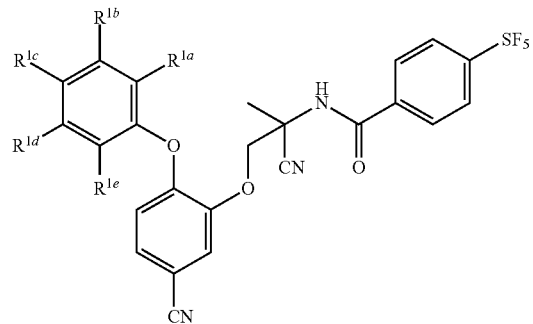

stereoisomer thereof, or veterinarily acceptable salt of said compound or stereoisomer thereof, or in combination with at least one additional veterinary agent, wherein: $R^1$, $R^2$, $R^3$, $R^4$, $R^5$, $R^{1a}$, $R^{1b}$, $R^{1c}$, $R^{1d}$, $R^{1e}$ are as described herein.

13 Claims, No Drawings

USE OF AMINOACETONITRILE DERIVATIVES AGAINST ENDOPARASITES

BACKGROUND OF THE INVENTION

The present invention relates to a method of treating a parasitic infection, particularly endoparasitic filarial infections, in animals, using certain pentafluorothio)benzamide-acetonitrile derivatives, hereinafter aminoacetonitrile (AAD) derivatives or compounds of the present invention.

There is a continuing need to provide new agents for the control of parasitic infections that present a threat to human and animal health. In particular, new agents are needed to manage parasitic infections in animals due to the increasing prevalence of parasites, and in particular nematodes, that are resistant or becoming resistant to many of the agents currently approved for this indication. For example, the heartworm, *Dirofilaria immitis*, is showing both phenotypic and genotypic signs of resistance to macrocyclic lactones, a usual course of treatment.

The aminoacetonitrile derivatives of the present invention have been previously described generically and as examples in U.S. Pat. No. 7,608,604, U.S. Pat. No. 7,622,500, and U.S. Pat. No. 8,168,681. Specific aminoacetonitrile derivatives and uses thereof as antiparasiticides in animals and/or plants have been disclosed in international patent application publications WO2010/056999, WO2008/144275, and WO2005/044784.

There remains a need for further compounds as alternative or improved therapeutic agents, particularly for the treatment of endoparasites, especially for filarial nematodes. Preferred compounds should be potent endoparasiticidal agents while presenting little or no toxicity to the host animal, and should exist in a physical form that is stable, non-hygroscopic and easily formulated. They should have high bioavailability, be metabolically stable and possess favorable pharmacokinetic properties. Heartworm data based on both the L4 larvae and microfilaria of *D. immitis* is presented herein.

SUMMARY OF THE INVENTION

This invention relates to a method of treating an endoparasitic infection in an animal, particularly filarial nematodes, comprising administering to said animal an effective amount of an aminoacetonitrile compound of Formula (I)

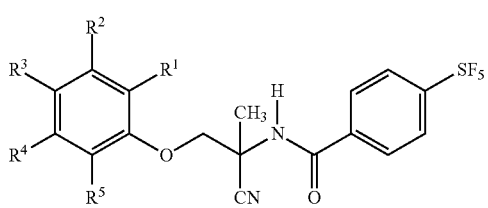

wherein $R^1$, $R^2$, $R^3$, $R^4$ and $R^5$ are each independently selected from hydrogen, halo, CN, $CF_3$, methyl, methoxy, —$OCF_3$, and —$SCH_3$. In another aspect of the invention, at least two of $R^1$, $R^2$, $R^3$, $R^4$ and $R^5$ are each independently hydrogen. In yet another aspect of the invention at least three of $R^1$, $R^2$, $R^3$, $R^4$ and $R^5$ are independently selected from hydrogen. In yet another aspect of the invention, $R^1$ and $R^2$ are each hydrogen and one of $R^3$ and $R^4$ are hydrogen and the other is CN. In yet another aspect of the invention, each of $R^1$, $R^2$, and $R^4$ are hydrogen, $R^3$ is CN, and $R^5$ is hydrogen, fluoro, chloro, CN, or $CF_3$. In yet another aspect of the invention, each of $R^1$, $R^2$, and $R^4$ is hydrogen, $R^3$ is CN, and $R^5$ is $CF_3$.

For all compound names listed herein, the number in parentheses after each compound name refers to the Example number which is equivalent to test compound number.

In yet another aspect of the invention is a method of treating an endoparasitic infection in an animal, particularly a filarial or microfilarial infection, comprising administering to said animal an effective amount of a Formula (I) compound selected from:

N-{1-cyano-2-[5-cyano-2-(trifluoromethyl)phenoxy]-1-methylethyl}-4-(pentafluorothio)benzamide (1);
N-[2-(2-chloro-4-cyanophenoxy)-1-cyano-1-methylethyl]-4-(pentafluorothio)benzamide (2);
N-{1-cyano-2-[5-cyano-2-(trifluoromethyl)phenoxy]-1-methylethyl}-4-(pentafluorothio)benzamide (3);
N-[2-(2-chloro-5-cyanophenoxy)-1-cyano-1-methylethyl]-4-(pentafluorothio)benzamide (4);
N-{1-cyano-2-[3-cyano-5-(trifluoromethyl)phenoxy]-1-methylethyl}-4-(pentafluorothio)benzamide (5);
N-[2-(3-chloro-4-cyanophenoxy)-1-cyano-1-methylethyl]-4-(pentafluorothio)benzamide (6);
N-{1-cyano-2-[4-cyano-2-(trifluoromethyl)phenoxy]-1-methylethyl}-4-(pentafluorothio)benzamide (7);
N-[1-cyano-2-(2,4-dichlorophenoxy)-1-methylethyl]-4-(pentafluorothio)benzamide (8);
N-[2-(3-chloro-5-cyanophenoxy)-1-cyano-1-methylethyl]-4-(pentafluorothio)-benzamide (9);
N-[2-(4-chlorophenoxy)-1-cyano-1-methylethyl]-4-(pentafluorothio)benzamide (10);
N-[2-(4-chloro-2-cyanophenoxy)-1-cyano-1-methylethyl]-4-(pentafluorothio)-benzamide (11);
N-[1-cyano-2-(2-cyanophenoxy)-1-methylethyl]-4-(pentafluorothio)benzamide (12);
N-[1-cyano-2-(4-iodophenoxy)-1-methylethyl]-4-(pentafluorothio)benzamide (13);
N-{1-cyano-1-methyl-2-[2-(trifluoromethyl)phenoxy]ethyl}-4-(pentafluorothio)-benzamide (14);
N-[1-cyano-2-(4-cyanophenoxy)-1-methylethyl]-4-(pentafluorothio)benzamide (15);
N-[2-(2-chlorophenoxy)-1-cyano-1-methylethyl]-4-(pentafluorothio)benzamide (16);
N-[2-(3-chloro-2-cyanophenoxy)-1-cyano-1-methylethyl]-4-(pentafluorothio)-benzamide (17);
N-[2-(2-chloro-4-fluorophenoxy)-1-cyano-1-methylethyl]-4-(pentafluorothio)-benzamide (18);
N-[1-cyano-2-(2-cyano-4-fluorophenoxy)-1-methylethyl]-4-(pentafluorothio)-benzamide (19);
N-[2-(4-chloro-2-fluorophenoxy)-1-cyano-1-methylethyl]-4-(pentafluorothio)-benzamide (20);
N-{2-[4-bromo-2-(trifluoromethyl)phenoxy]-1-cyano-1-methylethyl}-4-(pentafluorothio)benzamide (21);
N-{2-[2-chloro-4-(trifluoromethyl)phenoxy]-1-cyano-1-methylethyl}-4-(pentafluorothio)benzamide (22);
N-[2-(3-chloro-5-fluorophenoxy)-1-cyano-1-methylethyl]-4-(pentafluorothio)-benzamide (23);
N-[2-(3-chlorophenoxy)-1-cyano-1-methylethyl]-4-(pentafluorothio)benzamide (24);
N-[1-cyano-2-(3-cyano-5-fluorophenoxy)-1-methylethyl]-4-(pentafluorothio)-benzamide (25);
N-{1-cyano-2-[4-cyano-2-fluoro-6-(trifluoromethyl)phenoxy]-1-methylethyl}-4-(pentafluorothio)benzamide (26);
N-[2-(2-bromo-5-cyanophenoxy)-1-cyano-1-methylethyl]-4-(pentafluorothio)-benzamide (27);
N-[1-cyano-2-(3-cyanophenoxy)-1-methylethyl]-4-(pentafluorothio)benzamide (28);

N-[2-(2-bromo-4-cyanophenoxy)-1-cyano-1-methylethyl]-4-(pentafluorothio)-benzamide (29);
4-(2-cyano-2-{[4-(pentafluorothio)benzoyl]amino}propoxy)-3-(trifluoromethyl)-benzamide (30);
N-[2-(2-bromo-4-fluorophenoxy)-1-cyano-1-methylethyl]-4-(pentafluorothio)-benzamide (31);
N-[2-(4-bromo-2-fluorophenoxy)-1-cyano-1-methylethyl]-4-(pentafluorothio)-benzamide (32);
N-[2-(3-bromo-5-cyanophenoxy)-1-cyano-1-methylethyl]-4-(pentafluorothio)-benzamide (33);
N-[2-(2-chloro-3-fluorophenoxy)-1-cyano-1-methylethyl]-4-(pentafluorothio)-benzamide (34);
N-{1-cyano-2-[3-cyano-2-(trifluoromethyl)phenoxy]-1-methylethyl}-4-(pentafluorothio)-benzamide (35);
N-[2-(5-bromo-2-cyanophenoxy)-1-cyano-1-methylethyl]-4-(pentafluorothio)-benzamide (36);
N-[2-(2-bromo-3-cyanophenoxy)-1-cyano-1-methylethyl]-4-(pentafluorothio)-benzamide (37);
N-[1-cyano-2-(3,4-dichlorophenoxy)-1-methylethyl]-4-(pentafluorothio)benzamide (38);
N-[1-cyano-2-(2,5-dichlorophenoxy)-1-methylethyl]-4-(pentafluorothio)benzamide (39);
N-[1-cyano-2-(4-cyano-2-methylphenoxy)-1-methylethyl]-4-(pentafluorothio)-benzamide (40);
N-[1-cyano-2-(3-cyano-4-methoxyphenoxy)-1-methylethyl]-4-(pentafluorothio)-benzamide (41);
N-{1-cyano-2-[4-methoxy-2-(trifluoromethyl)phenoxy]-1-methyl ethyl}-4-(pentafluorothio)benzamide (42);
N-[1-cyano-2-(5-cyano-2-methylphenoxy)-1-methylethyl]-4-(pentafluorothio)benzamide (43);
N-[1-cyano-2-(2,6-dichlorophenoxy)-1-methylethyl]-4-(pentafluorothio)benzamide (44);
N-[2-(2-chloro-6-fluorophenoxy)-1-cyano-1-methylethyl]-4-(pentafluorothio)-benzamide (45);
3-chloro-4-(2-cyano-2-{[4-(pentafluorothio)benzoyl]amino}propoxy)benzamide (46);
4-cyano-2-(2-cyano-2-{[4-(pentafluorothio)benzoyl]amino}propoxy)benzamide (47);
3-cyano-5-(2-cyano-2-{[4-(pentafluorothio)benzoyl]amino}propoxy)benzamide (48);
N-[1-cyano-2-(2,4-dicyanophenoxy)-1-methylethyl]-4-(pentafluorothio)benzamide (49);
N-{2-[3-chloro-2-(trifluoromethyl)phenoxy]-1-cyano-1-methylethyl}-4-(pentafluorothio)benzamide (50);
N-{1-cyano-2-[4-cyano-2-(trifluoromethyl)phenoxy]-1-methylethyl}-4-(pentafluorothio)benzamide (51);
N-{(1S)1-cyano-2-[4-cyano-2-(trifluoromethyl)phenoxy]-1-methylethyl}-4-pentafluorothio)benzamide (51a);
N-[1-cyano-2-(4-cyano-2,6-difluorophenoxy)-1-methylethyl]-4-(pentafluorothio)-benzamide (52);
N-(1-cyano-1-methyl-2-{[4-(methylthio)benzyl]oxy}ethyl)-4-(pentafluorothio)benzamide (53);
N-[1-cyano-2-(2-cyano-4,6-difluorophenoxy)-1-methylethyl]-4-(pentafluorothio)-benzamide (54);
N-{1-cyano-2-[5-cyano-2-(trifluoromethoxy)phenoxy]-1-methyl ethyl}-4-(pentafluorothio)benzamide (55);
N-{1-cyano-2-[4-cyano-2-(trifluoromethoxy)phenoxy]-1-methylethyl}-4-(pentafluorothio)benzamide (56);
N-[2-(2-chloro-5-cyanophenoxy)-1-cyano-1-methylethyl]-4-(pentafluorothio)-benzamide (57);
N-[2-(2-bromo-4,5-difluorophenoxy)-1-cyano-1-methylethyl]-4-(pentafluorothio)benzamide (58); and
N-{1-cyano-2-[4,5-difluoro-2-(trifluoromethyl)phenoxy]-1-methylethyl}-4-(pentafluorothio)benzamide (59), stereoisomer thereof, or a veterinarily acceptable salt of said compound or stereoisomer thereof.

In yet another aspect of the invention is a method of treating an endoparasitic infection in an animal, particularly a filarial or microfilarial infection, comprising administering to said animal an effective amount of a Formula (I) compound selected from:

N-{1-cyano-2-[5-cyano-2-(trifluoromethyl)phenoxy]-1-methylethyl}-4-(pentafluorothio)benzamide (1);
N-{1-cyano-2-[5-cyano-2-(trifluoromethyl)phenoxy]-1-methylethyl}-4-(pentafluorothio)benzamide (3);
N-[2-(2-chloro-5-cyanophenoxy)-1-cyano-1-methylethyl]-4-(pentafluorothio)benzamide (4);
N-{1-cyano-2-[3-cyano-5-(trifluoromethyl)phenoxy]-1-methylethyl}-4-(pentafluorothio)benzamide (5);
N-{1-cyano-1-methyl-2-[2-(trifluoromethyl)phenoxy]ethyl}-4-(pentafluorothio)-benzamide (14);
N-[2-(3-chloro-2-cyanophenoxy)-1-cyano-1-methylethyl]-4-(pentafluorothio)-benzamide (17);
N-[2-(4-chloro-2-fluorophenoxy)-1-cyano-1-methylethyl]-4-(pentafluorothio)-benzamide (20);
N-{1-cyano-2-[4-cyano-2-fluoro-6-(trifluoromethyl)phenoxy]-1-methylethyl}-4-(pentafluorothio)benzamide (26);
N-[2-(2-bromo-5-cyanophenoxy)-1-cyano-1-methylethyl]-4-(pentafluorothio)-benzamide (27);
N-[2-(2-bromo-4-fluorophenoxy)-1-cyano-1-methylethyl]-4-(pentafluorothio)-benzamide (31);
N-[2-(5-bromo-2-cyanophenoxy)-1-cyano-1-methylethyl]-4-(pentafluorothio)-benzamide (36);
N-[1-cyano-2-(2,5-dichlorophenoxy)-1-methylethyl]-4-(pentafluorothio)benzamide (39);
N-{1-cyano-2-[4-cyano-2-(trifluoromethyl)phenoxy]-1-methylethyl}-4-(pentafluorothio)benzamide (51);
N-{(1S)1-cyano-2-[4-cyano-2-(trifluoromethyl)phenoxy]-1-methylethyl}-4-pentafluorothio)benzamide (51a); and
N-[2-(2-chloro-5-cyanophenoxy)-1-cyano-1-methylethyl]-4-(pentafluorothio)benzamide (57), stereoisomer thereof, or a veterinarily acceptable salt of said compound or stereoisomer thereof.

In yet another aspect of the invention is a method of treating an endoparasitic infection in an animal, particularly a filarial or microfilarial infection, comprising administering to said animal an effective amount of a Formula (I) compound selected from:

N-{1-cyano-2-[3-cyano-5-(trifluoromethyl)phenoxy]-1-methylethyl}-4-(pentafluorothio)benzamide (5);
N-[2-(2-bromo-5-cyanophenoxy)-1-cyano-1-methylethyl]-4-(pentafluorothio)-benzamide (27); and
N-{(1S)1-cyano-2-[4-cyano-2-(trifluoromethyl)phenoxy]-1-methylethyl}-4-pentafluorothio)benzamide (51a), stereoisomer thereof, or a veterinarily acceptable salt of said compound or stereoisomer thereof.

In yet another aspect of the invention, is a method of treating an endoparasitic infection in an animal, particularly a filarial or microfilarial infection, comprising administering to said animal an effective amount of an aminoacetonitrile of Formula (II)

(II)

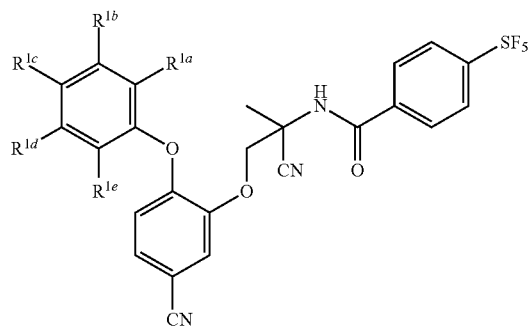

wherein $R^{1a}$, $R^{1b}$, $R^{1c}$, $R^{1d}$, and $R^{1e}$ are each independently selected from the group consisting of hydrogen, halo, $CF_3$, —$OCH_3$, methyl, and hydroxyl.

In yet another aspect of the invention, are compounds of Formula (II) selected from the group consisting of:
N-[1-cyano-2-(5-cyano-2-phenoxyphenoxy)-1-methylethyl]-4-(pentafluorothio)benzamide (60);
N-{1-cyano-2-[5-cyano-2-(4-fluorophenoxy)phenoxy]-1-methylethyl}-4-(pentafluorothio)benzamide (61);
N-{2-[2-(4-chloro-2-fluorophenoxy)-5-cyanophenoxy]-1-cyano-1-methylethyl}-4-(pentafluorothio)benzamide (62);
N-{2-[2-(2-chloro-4-fluorophenoxy)-5-cyanophenoxy]-1-cyano-1-methylethyl}-4-(pentafluorothio)benzamide (63);
N-{2-[2-(4-chlorophenoxy)-5-cyanophenoxy]-1-cyano-1-methylethyl}-4-(pentafluorothio)benzamide (64);
N-{1-cyano-2-[5-cyano-2-(2,4-dichlorophenoxy)phenoxy]-1-methylethyl}-4-(pentafluorothio)benzamide (65);
N-{1-cyano-2-[5-cyano-2-(4-methoxyphenoxy)phenoxy]-1-methylethyl}-4-(pentafluorothio)benzamide (66);
N-(1-cyano-2-{5-cyano-2-[4-(trifluoromethyl)phenoxy]phenoxy}-1-methylethyl)-4-(pentafluorothio)benzamide (67);
N-{1-cyano-2-[5-cyano-2-(3-methoxyphenoxy)phenoxy]-1-methylethyl}-4-(pentafluorothio)benzamide (68);
N-{1-cyano-2-[5-cyano-2-(2-methoxyphenoxy)phenoxy]-1-methylethyl}-4-(pentafluorothio)benzamide (69);
N-{1-cyano-2-[5-cyano-2-(4-fluoro-2-methylphenoxy)phenoxy]-1-methylethyl}-4-(pentafluorothio)benzamide (70);
N-{2-[2-(2-chloro-4-methylphenoxy)-5-cyanophenoxy]-1-cyano-1-methylethyl}-4-(pentafluorothio)benzamide (71);
N-{1-cyano-2-[5-cyano-2-(2,4-dimethylphenoxy)phenoxy]-1-methylethyl}-4-(pentafluorothio)benzamide (72);
N-{1-cyano-2-[5-cyano-2-(2-fluorophenoxy)phenoxy]-1-methylethyl}-4-(pentafluorothio)benzamide (73);
N-{1-cyano-2-[5-cyano-2-(2-fluoro-4-methoxyphenoxy)phenoxy]-1-methylethyl}-4-(pentafluorothio)benzamide (74);
N-{2-[2-(2-chloro-4-methoxyphenoxy)-5-cyanophenoxy]-1-cyano-1-methylethyl}-4-(pentafluorothio)benzamide (75);
N-{1-cyano-2-[5-cyano-2-(2,3-difluoro-4-methoxyphenoxy)phenoxy]-1-methylethyl}-4-(pentafluorothio)benzamide (76);
N-{1-cyano-2-[5-cyano-2-(2,6-difluoro-4-methoxyphenoxy)phenoxy]-1-methylethyl}-4-(pentafluorothio)benzamide (77);
N-{1-cyano-2-[5-cyano-2-(3,5-difluoro-4-methoxyphenoxy)phenoxy]-1-methylethyl}-4-(pentafluorothio)benzamide (78); and
N-{1-cyano-2-[5-cyano-2-(4-hydroxy-2-methoxyphenoxy)phenoxy]-1-methylethyl}-4-(pentafluorothio)benzamide (79), stereoisomer thereof, or a veterinarily acceptable salt thereof, wherein said compound is effective in treating said endoparasitic infection.

In yet another aspect of the invention are compounds of Formula (II) selected from the group consisting of:
N-[1-cyano-2-(5-cyano-2-phenoxyphenoxy)-1-methylethyl]-4-(pentafluorothio)benzamide (60);
N-{1-cyano-2-[5-cyano-2-(4-fluorophenoxy)phenoxy]-1-methylethyl}-4-(pentafluorothio)benzamide (61);
N-{2-[2-(4-chloro-2-fluorophenoxy)-5-cyanophenoxy]-1-cyano-1-methylethyl}-4-(pentafluorothio)benzamide (62);
N-{2-[2-(2-chloro-4-fluorophenoxy)-5-cyanophenoxy]-1-cyano-1-methylethyl}-4-(pentafluorothio)benzamide (63);
N-{2-[2-(4-chlorophenoxy)-5-cyanophenoxy]-1-cyano-1-methylethyl}-4-(pentafluorothio)benzamide (64);
N-{1-cyano-2-[5-cyano-2-(2,4-dichlorophenoxy)phenoxy]-1-methylethyl}-4-(pentafluorothio)benzamide (65);
N-{1-cyano-2-[5-cyano-2-(4-methoxyphenoxy)phenoxy]-1-methylethyl}-4-(pentafluorothio)benzamide (66);
N-(1-cyano-2-{5-cyano-2-[4-(trifluoromethyl)phenoxy]phenoxy}-1-methylethyl)-4-(pentafluorothio)benzamide (67);
N-{1-cyano-2-[5-cyano-2-(3-methoxyphenoxy)phenoxy]-1-methylethyl}-4-(pentafluorothio)benzamide (68);
N-{1-cyano-2-[5-cyano-2-(2-methoxyphenoxy)phenoxy]-1-methylethyl}-4-(pentafluorothio)benzamide (69);
N-{1-cyano-2-[5-cyano-2-(4-fluoro-2-methylphenoxy)phenoxy]-1-methylethyl}-4-(pentafluorothio)benzamide (70);
N-{2-[2-(2-chloro-4-methylphenoxy)-5-cyanophenoxy]-1-cyano-1-methylethyl}-4-(pentafluorothio)benzamide (71);
N-{1-cyano-2-[5-cyano-2-(2,4-dimethylphenoxy)phenoxy]-1-methylethyl}-4-(pentafluorothio)benzamide (72);
N-{2-[2-(2-chloro-4-methoxyphenoxy)-5-cyanophenoxy]-1-cyano-1-methylethyl}-4-(pentafluorothio)benzamide (75); and
N-{1-cyano-2-[5-cyano-2-(3,5-difluoro-4-methoxyphenoxy)phenoxy]-1-methylethyl}-4-(pentafluorothio)benzamide (78), stereoisomer thereof, or a veterinarily acceptable salt thereof, wherein said compound is effective in treating said endoparasitic infection.

In yet another aspect of the invention are compounds of Formula (II) selected from the group consisting of:
N-{1-cyano-2-[5-cyano-2-(4-fluorophenoxy)phenoxy]-1-methylethyl}-4-(pentafluorothio)benzamide (61);
N-{2-[2-(4-chloro-2-fluorophenoxy)-5-cyanophenoxy]-1-cyano-1-methylethyl}-4-(pentafluorothio)benzamide (62);
N-{2-[2-(4-chlorophenoxy)-5-cyanophenoxy]-1-cyano-1-methylethyl}-4-(pentafluorothio)benzamide (64);
N-(1-cyano-2-{5-cyano-2-[4-(trifluoromethyl)phenoxy]phenoxy}-1-methylethyl)-4-(pentafluorothio)benzamide (67);
N-{2-[2-(2-chloro-4-methylphenoxy)-5-cyanophenoxy]-1-cyano-1-methylethyl}-4-(pentafluorothio)benzamide (71);
N-{1-cyano-2-[5-cyano-2-(2,4-dimethylphenoxy)phenoxy]-1-methylethyl}-4-(pentafluorothio)benzamide (72); and N-{1-cyano-2-[5-cyano-2-(3,5-difluoro-4-methoxyphenoxy)phenoxy]-1-methylethyl}-4-(pentafluorothio)benzamide (78), stereoisomer thereof, or a veterinarily acceptable salt thereof, wherein said compound is effective in treating said endoparasitic infection.

In yet another aspect of the invention is a method of treating an endoparasitic infection in an animal, particularly a filarial or microfilarial infection, comprising administering to said animal an effective amount of an aminoacetonitrile homolog selected from the group consisting of N-[1-(7-chloro-5-cyano-2,3-dihydro-1-benzofuran-2-yl)-1-cyanoethyl]-4-(pentafluorothio)benzamide (80);
N-{1-cyano-1-methyl-2-[4-pyridin-4-yl-2-(trifluoromethyl)phenoxy]ethyl}-4-(pentafluorothio)benzamide (81);
N-{1-cyano-1-methyl-2-[4-pyridin-3-yl-2-(trifluoromethyl)phenoxy]ethyl}-4-(pentafluorothio)benzamide (82);
N-{1-cyano-1-[5-cyano-7-(trifluoromethyl)-2,3-dihydro-1-benzofuran-2-yl]ethyl}-4-(pentafluorothio)benzamide (83);
N-(1-cyano-1-methyl-2-{[4-(trifluoromethyl)benzyl]oxy}ethyl)-4-(pentafluorothio)benzamide (84);
N-{2-[(2-chloro-4-fluorobenzyl)oxy]-1-cyano-1-methylethyl}-4-(pentafluorothio)benzamide (85);
N-{1-cyano-2-[(3,4-difluorobenzyl)oxy]-1-methylethyl}-4-(pentafluorothio)benzamide (86);
N-(1-cyano-2-{[4-cyano-2-(trifluoromethyl)benzyl]oxy}-1-methylethyl)-4-(pentafluorothio)benzamide (87);
N-{1-cyano-2-[5-cyano-2-(pyridin-3-yloxy)phenoxy]-1-methylethyl}-4-(pentafluorothio)benzamide (88);
N-{1-cyano-2-[4-cyano-2-(trifluoromethyl)phenyl]-1-methylethyl}-4-(pentafluorothio)benzamide (89); and
N-[2-(2-chloro-4-cyanophenyl)-1-cyano-1-methylethyl]-4-(pentafluorothio)benzamide (90), stereoisomer thereof, or a veterinarily acceptable salt thereof, wherein said compound is effective in treating said endoparasitic infection.

In yet another aspect of the invention is an aminoacetonitrile homolog selected from the group consisting of:

N-[1-(7-chloro-5-cyano-2,3-dihydro-1-benzofuran-2-yl)-1-cyanoethyl]-4-(pentafluorothio)benzamide (80);
N-{1-cyano-1-methyl-2-[4-pyridin-4-yl-2-(trifluoromethyl)phenoxy]ethyl}-4-(pentafluorothio)benzamide (81);
N-{1-cyano-1-methyl-2-[4-pyridin-3-yl-2-(trifluoromethyl)phenoxy]ethyl}-4-(pentafluorothio)benzamide (82);
N-{1-cyano-1-[5-cyano-7-(trifluoromethyl)-2,3-dihydro-1-benzofuran-2-yl]ethyl}-4-(pentafluorothio)benzamide (83);
N-(1-cyano-1-methyl-2-{[4-(trifluoromethyl)benzyl]oxy}ethyl)-4-(pentafluorothio)benzamide (84);
N-{2-[(2-chloro-4-fluorobenzyl)oxy]-1-cyano-1-methylethyl}-4-(pentafluorothio)benzamide (85);
N-{1-cyano-2-[(3,4-difluorobenzyl)oxy]-1-methylethyl}-4-(pentafluorothio)benzamide (86);
N-(1-cyano-2-{[4-cyano-2-(trifluoromethyl)benzyl]oxy}-1-methylethyl)-4-(pentafluorothio)benzamide (87);
N-{1-cyano-2-[5-cyano-2-(pyridin-3-yloxy)phenoxy]-1-methylethyl}-4-(pentafluorothio)benzamide (88);
N-{1-cyano-2-[4-cyano-2-(trifluoromethyl)phenyl]-1-methylethyl}-4-(pentafluorothio)benzamide (89); and
N-[2-(2-chloro-4-cyanophenyl)-1-cyano-1-methylethyl]-4-(pentafluorothio)benzamide (90), stereoisomer thereof, or a veterinarily acceptable salt thereof, wherein said compound is effective in treating said endoparasitic infection.

In a further aspect, the present invention provides a Formula (I) compound, Formula (II) compound, or aminoacetonitrile homolog, stereoisomer thereof, or a veterinarily acceptable salt of said Formula (I) compound, Formula (II) compound, or aminoacetonitrile homolog or stereoisomer thereof, for use as a medicament for the treatment of an endoparasitic infection in an animal, particularly a filarial or microfilarial infection.

In a further aspect, the present invention provides for a method of treatment of an endoparasitic infection in a human, particularly a filarial or microfilarial infection, comprising treating the human with an effective amount of a Formula (I) compound, Formula (II) compound, or aminoacetonitrile homolog, stereoisomer thereof, or a veterinarily acceptable salt of said compound or stereoisomer thereof.

In a further aspect, the present invention provides for a method of treatment of an endoparasitic infection in a companion animal, particularly a filarial or microfilarial infection, comprising treating the companion animal with an effective amount of a Formula (I) compound, Formula (II) compound, or aminoacetonitrile homolog, stereoisomer thereof, or a veterinarily acceptable salt of said compound or stereoisomer thereof.

In a further aspect, the present invention provides a pharmaceutical composition comprising a Formula (I) compound, Formula (II) compound, or aminoacetonitrile homolog, stereoisomer thereof, or a veterinarily acceptable salt of said compound or stereoisomer thereof, and veterinarily acceptable carrier for treating an endoparasitic infection in an animal, particularly a filarial or microfilarial infection.

DEFINITIONS

For purposes of the present invention, as described and claimed herein, the following terms and phrases are defined as follows:

"Additional veterinary agent(s)" as used herein, unless otherwise indicated, refers to other veterinary or pharmaceutical compounds or products that provide a therapeutically effective amount of said agents that are useful for the treatment of a parasitic infection in an animal, as described herein.

"Animal(s)", as used herein, unless otherwise indicated, refers to an individual animal that is a mammal. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, ferrets, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine.

"Compound(s) of the present invention", as used herein, unless otherwise indicated, refers to Formula (I) compounds, Formula (II) compounds, and aminoacetonitrile homologs thereof, stereoisomers of the Formula (I), Formula (II) and aminoacetonitrile homologs thereof, and veterinarily acceptable salts of said Formula (I) compounds, Formula (II) compound(s), or aminoacetonitrile homologs.

"Effective amount", as used herein, unless otherwise indicated, refers to an amount of the compounds of the present invention that (i) treat the particular parasitic infection, (ii) attenuates, ameliorates, or eliminates one or more symptoms of the particular parasitic infection, or (iii) prevents or delays the onset of one or more symptoms of the particular parasitic infection described herein.

"Ectoparasite(s)", as used herein, unless otherwise indicated, refers to both adult and larval stages of parasites that live or feed on the outside of the body of its host. Non-limiting examples of ectoparasites include: ticks, mites, fleas, midges, mosquitoes, lice, biting flies, and the like.

"Endoparasite(s)", as used herein, unless otherwise indicated, refers to both adult and larval stages of parasites that live within the body of its host. Non-limiting examples of endoparasites include: roundworms, heartworms, whipworms, lungworms, and the like.

"Filarial", as used herein, unless otherwise indicated, refers to any of various slender, threadlike nematodes of the superfamily Filarioidea that are parasitic in animals and are often transmitted as larvae by mosquitoes and other biting insects. The adult form of the nematode lives in the blood and lymphatic tissues of its host, causing inflammation and obstruction that can eventually lead to death of the host. The microfilarial or larval stages of these parasites can live in a vector (i.e., mosquito, biting fly, and the like) before being transferred to the host from the vector.

"Halogen" or "halo", as used herein, unless otherwise indicated, refers to fluorine, chlorine, bromine and iodine.

"Treatment", "treating", and the like, as used herein, unless otherwise indicated, refers to reversing, alleviating, or inhibiting the parasitic infection, infection, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection. Thus, treatment can refer to administration of the compounds of the present invention to an animal that is not at the time of administration afflicted with the infection. Treating also encompasses preventing the recurrence of an infection or of symptoms associated therewith as well as references to "control" (e.g., kill, repel, expel, incapacitate, deter, eliminate, alleviate, minimize, and eradicate).

"Veterinarily acceptable" as used herein, unless otherwise indicated, indicates that the substance or composition must be compatible chemically and/or toxicologically, with the other ingredients comprising a formulation, composition, and/or the animal being treated therewith. The term is also interchangeable with the term "pharmaceutically" acceptable. The term "pharmaceutically acceptable" as used in this specification, for example with reference to salts and stereoisomers, is analogous to the term "veterinarily acceptable".

DETAILED DESCRIPTION

The present invention provides for a method of treating a parasitic infection, preferably an endoparasitic infection in an animal, particularly a filarial or microfilarial infection, comprising administering an effective amount of a Formula (I) compound, Formula (II) compound, or aminoacetonitrile homolog, stereoisomer, or veterinarily acceptable salt of said compound/homolog thereof. Preferably, the endoparasitic infection is caused from a filarial species of nematode and the animal is a companion animal.

The Formula (I) compounds can be prepared as described in U.S. Pat. No. 7,608,604. The Formula (II) compounds can be prepared as described in U.S. Pat. No. 8,168,681. In addition, the aminoacetonitrile homologs can be prepared according to methods described in U.S. Pat. No. 7,608,604, U.S. Pat. No. 8,168,681, and U.S. Pat. No. 7,622,500. The US patents and WO patent publications recited in this application are herein incorporated by reference in their entirety.

The compounds of the present invention, stereoisomers, and veterinarily acceptable salts thereof, are generally known as nicotinic acetylcholine esterase agonists and therefore are of value in the treatment of endoparasites that possess the specific receptors. In particular, it is known that the AADs bind to the acetylcholine receptor subunits ACR-23 and MPTL-1 in nematodes. Rufener, L., et. al., Phylogenomics of Ligand-Gated Ion Channels Predicts Monepantel Effect, PLoS Pathogens, Vol. 6, Issue 9, September 2010. Interestingly, these acetylcholine subunits are not observed in *Dirofilaria*, yet the Formula (I) compounds or aminoacetonitrile homologs of the instant invention are useful for treating filarial infections. Current heartworm therapies include the use of a macrocyclic lactone, for example, avermectin or ivermectin, which macrocyclic lactones selectively bind to glutamate-gated chloride channels.

The Formula (I) compounds, Formula (II) compounds, or aminoacetonitrile homologs, stereoisomer of said compound/homolog thereof, or a veterinarily acceptable salt of said compound/homolog thereof, can be administered by oral, topical, or parenteral routes. In general, these compounds are most desirably administered in dosages ranging from about 1.0 mg up to about 100 mg per month, although variations will necessarily occur depending upon the weight and condition of the animal being treated and the particular route of administration chosen. However, a dosage level that is in the range of about 0.1 mg to about 50 mg per kg of body weight per day is most desirably employed. Variations may nevertheless occur depending upon the species of animal being treated and its individual response to said medicament, as well as on the type of veterinary formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day. Further, dosage amounts can be adjusted to account for single monthly, semi-annually, or annual administration.

The compounds of the present invention, stereoisomer thereof, or a veterinarily acceptable salt thereof, can be administered alone or in combination with veterinarily acceptable carriers or diluents by either of the routes indicated herein, and such administration may be carried out in single or multiple doses. The compounds of the present invention can be administered in a wide variety of different dosage forms, i.e., they may be combined with various veterinarily acceptable inert carriers in the form of tablets, capsules, hard/soft chews, aqueous suspensions, injectable solutions, elixirs, syrups, and the like. Such carriers include solid diluents or fillers, sterile aqueous media and various non-toxic organic solvents. Moreover, oral veterinary compositions can be suitably flavored. In general, the therapeutic compounds of this invention are present in such dosage forms at concentration levels ranging from about 50% to about 70% by weight.

The Formula (I) compounds, Formula (II) compounds, or aminoacetonitrile homologs, stereoisomer of said compound/homolog thereof, or a veterinarily acceptable salt of said compound/homolog thereof, are particularly useful for the control of endoparasitic infections in companion animals. In one embodiment, the Formula (I) compounds, Formula (II) compounds, or aminoacetonitrile homologs, stereoisomers of said compound/homolog thereof, or veterinarily acceptable salt of said compound/homolog thereof, are useful for treating endoparasiticidal infection from filarial nematodes. The filarial nematodes are in the Order, Spirurida, super-family Filarioidea, and Onchocercidae Family. Non-limiting examples of filarial nematodes within the Onchocercidae Family include the genus *Brugia* spp. (i.e., *B. malayi, B. pahangi, B. timori*, and the like), *Wuchereria* spp. (i.e., *W. bancrofti*, and the like), *Dirofilaria* spp. (*D. immitis, D. repens, D. ursi, D. tenuis, D. spectans, D. lutrae*, and the like),

*Dipetalonema* spp. (i.e., *D. reconditum, D. repens*, and the like), *Onchocerca* spp. (i.e., *O. gibsoni, O. gutturosa, O. volvulus*, and the like), *Elaeophora* spp. (*E. bohmi, E. elaphi, E. poeli, E. sagitta, E. schneideri*, and the like), *Mansonella* spp. (i.e., *M. ozzardi, M. perstans*, and the like), and *Loa* spp. (i.e., *L. loa*).

In another aspect of the invention, the Formula (I) compounds, Formula (II) compounds, aminoacetonitrile homologs, stereoisomers of said compound/homolog, or veterinarily acceptable salt of said compound/homolog thereof, are useful for treating endoparasiticidal infection from filarial nematodes within the genus *Dirofilaria* (i.e., *D. immitis, D. repens, D. ursi, D. tenuis*, and the like).

In another aspect of the invention, the Formula (I) compounds, Formula (II) compounds, aminoacetonitrile homologs, stereoisomers of said compound/homolog, or veterinarily acceptable salt of said compound/homolog thereof, are useful for treating endoparasiticidal infection of *D. immitis*.

In another embodiment, the Formula (I) compounds, Formula (II) compounds, aminoacetonitrile homologs, stereoisomers of said compound/homolog, or veterinarily acceptable salt of said compound/homolog thereof, are useful for treating endoparasiticidal infection from lungworms, for example, *Angiostrongylus vasorum* and *Aelurostrongylus abstrusus*.

In yet another aspect of the invention is the formation of parasiticidal compositions which comprise the Formula (I) compounds, Formula (II) compounds, aminoacetonitrile homologs, stereoisomers of said compound/homolog, or veterinarily acceptable salt of said compound/homolog thereof. The composition of the invention can also be in a variety of forms which include, but are not limited to, oral formulations, injectable formulations, and topical, dermal or subdermal formulations. The formulations are intended to be administered to an animal.

The animal may be human or non-human mammal. Non-human mammals include livestock (e.g., cattle, sheep, swine, goats, deer, bison, and the like) and companion animals (e.g., equine, ferrets, dogs and cats).

The Formula (I) compounds, Formula (II) compounds, aminoacetonitrile homologs, stereoisomers of said compound/homolog, or veterinarily acceptable salt of said compound/homolog thereof, may be administered by any suitable route. Examples of suitable routes of administration include oral, topical and parenteral administration. The choice of the route will depend on the species of the host animal and the nature of the parasitic infection. For example, oral administration might be preferred in the case of a human or companion animal host, or for the treatment of endoparasites, while topical administration might be more convenient for treating large numbers of livestock animals such as a herd of cattle.

The Formula (I) compounds, Formula (II) compounds, aminoacetonitrile homologs, stereoisomers of said compound/homolog, or veterinarily acceptable salt of said compound/homolog thereof, may be administered alone or in a formulation appropriate rally, they will be administered as a formulation in association with one or more veterinary acceptable excipients.

The Formula (I) compounds, Formula (II) compounds, aminoacetonitrile homologs, stereoisomers of said compound/homolog, or veterinarily acceptable salt of said compound/homolog thereof, may be administered as crystalline or amorphous products, for example, spray-dried dispersions or as produced by melt-extrusion or nano-milling. They may be obtained, for example, as solid plugs, powders, or films (for example, rapid dissolving or mucoadhesive films) by methods such as precipitation, crystallization, freeze drying, or spray drying, or evaporative drying. Microwave or radio frequency drying may be used for this purpose.

The methods by which the Formula (I) compounds, Formula (II) compounds, aminoacetonitrile homologs, stereoisomers of said compound/homolog, or veterinarily acceptable salt of said compound/homolog thereof, may be administered include oral administration by capsule, bolus, tablet, powders, lozenges, chews, multi and nanoparticulates, gels, solid solution, films, sprays, or liquid formulation. Liquid forms include suspensions, solutions, syrups, drenches and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. Oral drenches are commonly prepared by dissolving or suspending the active ingredient in a suitable medium.

Thus compositions useful for oral administration may be prepared by mixing the active ingredient with a suitable finely divided diluent and/or disintegrating agent and/or binder, and/or lubricant etc. Other possible ingredients include antioxidants, colourants, flavouring agents, preservatives and taste-masking agents.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the compound of the present invention may be combined with various sweetening or flavoring agents, coloring matter or dyes, and, if so desired, emulsifying and/or suspending agents as well, together with such diluents as water, ethanol, propylene glycol, glycerin and various like combinations thereof.

Binders are generally used to impart cohesive qualities to a tablet formulation. Examples of suitable binders for use herein include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Examples of diluents include lactose (monohydrate, spray-dried monohydrate, anhydrous and the like), mannitol, xylitol, dextrose, sucrose, sorbitol, microcrystalline cellulose, starch and dibasic calcium phosphate dihydrate.

Oral formulations may also optionally comprise surface active agents, such as sodium lauryl sulfate and polysorbate 80, and glidants such as silicon dioxide and talc.

Lubricants include magnesium stearate, calcium stearate, zinc stearate, sodium stearyl fumarate, and mixtures of magnesium stearate with sodium lauryl sulphate.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The Formula (I) compounds, Formula (II) compounds, aminoacetonitrile homologs, stereoisomers of said compound/homolog, or veterinarily acceptable salt of said compound/homolog thereof, may be administered topically to the skin, that is dermally or transdermally. The compounds/homologs may also be administered via the mucosa or mucous membranes. Typical formulations for this purpose include pour-on, spot-on, dip, spray, mousse, shampoo, powder formulation, gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J. Pharm Sci, 88 (10), 955-958 by Finnin and Morgan (October 1999). Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal.

Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.01 to 10% by weight of the active ingredient. These formulations may be self-preserving, self-sterilizing or may be non-sterile to which preservatives may be optionally added.

Equally suitably the Formula (I) compounds, Formula (II) compounds, aminoacetonitrile homologs, stereoisomers of said compound/homolog, or veterinarily acceptable salt of said compound/homolog thereof, can be administered parenterally. Suitable routes for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as powdered a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The solubility of the Formula (I) compounds, Formula (II) compounds, aminoacetonitrile homologs, stereoisomers of said compound/homolog, or veterinarily acceptable salt of said compound/homolog thereof, used in the preparation of parenteral solutions may be increased by the use of appropriate formulation techniques, such as the incorporation of solubility-enhancing agents.

Such formulations are prepared in a conventional manner in accordance with standard veterinary or medicinal practice. These formulations will vary with regard to the weight of active compound contained therein, depending on the species of host animal to be treated, the severity and type of infection and the body weight of the host.

Formulations may be immediate release or be designed to have a controlled or modified release profile. Modified release formulations include those formulations which have a delayed-, sustained-, pulsed-, targeted, or programmed release. Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). Alternatively, compounds of the invention may be formulated as a solid, semi-solid, or thixotropic liquid for administration as an implanted depot providing modified release of the active compound. Examples of such formulations include drug-coated stents and PGLA microspheres.

As an alternative, the Formula (I) compounds, Formula (II) compounds, aminoacetonitrile homologs, stereoisomers of said compound/homolog, or veterinarily acceptable salt of said compound/homolog thereof, may be administered to a non-human animal with the feedstuff and for this purpose a concentrated feed additive or premix may be prepared for mixing with the normal animal feed.

The Formula (I) compounds, Formula (II) compounds, aminoacetonitrile homologs, stereoisomers of said compound/homolog, or veterinarily acceptable salt of said compound/homolog thereof, may advantageously be used in combination with one or more additional veterinary agents, including, but not limited to, further antiparasitic agents.

Examples of antiparasitic agents that may be used in combination with the Formula (I) compounds, Formula (II) compounds, aminoacetonitrile homologs, stereoisomers of said compound/homolog, or veterinarily acceptable salt of said compound/homolog thereof; include endoparasiticides, fasciolicides and ectoparasiticides.

In one embodiment of the invention, the Formula (I) compounds, Formula (II) compounds, aminoacetonitrile homologs, stereoisomers of said compound/homolog, or veterinarily acceptable salt of said compound/homolog thereof, are used in combination with at least one other antiparasitic agent. The other antiparasitic agent(s) may be ectoparasiticides and/or endoparasiticides. Such a combination may reduce the likelihood of resistance developing and may expand the scope of target parasites. Non-limiting examples of other antiparasitic agents that can be combined with the AAD's of the present invention include:

- the macrocyclic lactone class of compounds (for example, ivermectin, avermectin, abamectin, emamectin, eprinomectin, doramectin, selamectin, moxidectin, nemadectin, milbemycin, milbemycin oxime, milbemycin derivatives, and the like);
- benzimidazoles (for example, albendazole, cambendazole, fenbendazole, flubendazole, mebendazole, oxfendazole, oxibendazole, parbendazole, thiabendazole, febantel, netobimin, and the like);
- imidazothiazoles and tetrahydropyrimidines (for example, tetramisole, levamisole, pyrantel pamoate, oxantel, morantel, and the like);
- derivatives and analogues of the paraherquamide/marcfortine class of anthelmintic agents, particularly 2-desoxoparaherquamide;
- nitroscanate;
- antiparasitic isoxazolines (for example, those described in WO2010/025998, WO2009/003075, WO2007/079162, U.S. Pat. No. 7,662,972, U.S. Pat. No. 7,947,715, U.S. Provisional Applications 61/490,811 and 61/490,804;

and in particular, 5-(3,5-dichloro-4-fluorophenyl)-3-(4-{3-fluoro-1-[(methylsulfonyl)acetyl]azetidin-3-yl}phenyl)-5-(trifluoromethyl)-4,5-dihydroisoxazole; 1-(3-fluoro-3-(4-(5-(3,4,5-trichlorophenyl)-5-(trifluoromethyl)-4,5-dihydroisoxazol-3-yl)phenyl)azetidin-1-yl)-2-(methylsulfonyl)ethanone; 1-(3-(4-(5-(3,5-dichlorophenyl)-5-(trifluoromethyl)-4,5-dihydroisoxazol-3-yl)phenyl)-3-fluoroazetidin-1-yl)-2-(methylsulfonyl)ethanone; (3-(4-(5-(3,5-dichloro-4-fluorophenyl)-5-(trifluoromethyl)-4,5-dihydroisoxazol-3-yl)phenyl)-3-fluoroazetidin-1-yl)(1,1-dioxidothietan-3-yl)methanone; (1,1-dioxidothietan-3-yl)(3-fluoro-3-(4-(5-(3,4,5-trichlorophenyl)-5-(trifluoromethyl)-4,5-dihydroisoxazol-3-yl)phenyl)azetidin-1-yl)methanone; (3-(4-(5-(3,5-dichlorophenyl)-5-(trifluoromethyl)-4,5-dihydroisoxazol-3-yl)phenyl)-3-fluoroazetidin-1-yl)(1,1-dioxidothietan-3-yl)methanone; 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 2-(methylsulfonyl)-1-(5'-(5-(3,4,5-trichlorophenyl)-5-(trifluoromethyl)-4,5-dihydroisoxazol-3-yl)-3'H-spiro[azetidine-3,1'-isobenzofuran]-1-yl)ethanone; 1-(5'-(5-(3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 4-(5-(3,5-dichlorophenyl)-5-(trifluoromethyl)-4,5-dihydroisoxazol-3-yl)-N-(2-oxo-2-((2,2,2-trifluoroethyl)amino)ethyl)-1-naphthamide; 4-(5-(3,5-dichlorophenyl)-5-(trifluoromethyl)-4,5-dihydroisoxazol-3-yl)-2-methyl-N-(2-oxo-2-((2,2,2-trifluoroethyl)amino)ethyl)benzamide; (S)-2-((4-(5-(3,5-dichlorophenyl)-5-(trifluoromethyl)-4,5-dihydroisoxazol-3-yl)-2-methylphenyl)sulfonyl)-N-(2,2,2-trifluoroethyl)acetamide; 4-(5-(3,5-dichloro-4-fluorophenyl)-5-(trifluoromethyl)-4,5-dihydroisoxazol-3-yl)-N-(1,1-dioxidothietan-3-yl)-2-methylbenzamide; 4-(5-(3,5-dichlorophenyl)-5-(trifluoromethyl)-4,5-dihydrofuran-3-yl)-N-(1,1-dioxidothietan-3-yl)-2-methylbenzamide; and 4-(5-(3,5-dichlorophenyl)-5-(trifluoromethyl)-4,5-dihydroisoxazol-3-yl)-N-(1,1-dioxidothietan-3-yl)-1-naphthamide; 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

octopaminergic agonists (for example, demiditraz, amitraz, and the like);

derivatives and analogues of the general class of dioxomorpholine antiparasitic agents as described in WO199615121;

cyclic depsipeptides (such as those described in WO1996/11945, WO1993/19053, WO1993/25543, EP626375, EP382173, WO1994/19334, EP382173, and EP503538, and particularly emodepside).

aryl pyrazoles (such as fipronil, pyriprole, pyrafluprole and the like);

pyrethrins and pyrethroids;

organophosphates;

spiroindolines;

tetracyclines (for example, doxycycline);

insect growth regulators (such as methoprene, hydroprene, pyriproxyfen, lufenuron, diflubenzuron, and the like);

spiroketoenol insecticides (such as spiromesifen and the like);

ecdysone agonists (such as tebufenozide and the like);

spinosyns (such as spinosad, spinetoram and the like, especially spinetoram);

neonicotinoids (such as imidacloprid, dinotefuran and the like) and other insecticides (such as metaflumizone, flubendiamide, chlorantraniliprole, indoxacarb, indoxacarb derivatives, pyridalyl, pyrimidifen, piperazine, diethylcarbamazine, melarsomine dihydrochloride, nitenpyram, praziquantel, and pyrifluquinazon).

In one embodiment, the Formula (I) compounds, Formula (II) compounds, aminoacetonitrile homologs, stereoisomers of said compound/homolog, or veterinarily acceptable salt of said compound/homolog thereof, are used in combination with a macrocyclic lactone anthelmintic agent selected from ivermectin, avermectin, abamectin, emamectin, eprinomectin, doramectin, selamectin, moxidectin, nemadectin and milbemycin oxime.

In another embodiment, the Formula (I) compounds, Formula (II) compounds, aminoacetonitrile homologs, stereoisomers of said compound/homolog, or veterinarily acceptable salt of said compound/homolog thereof, are used in combination with a benzimidazole anthelmintic agent selected from albendazole, cambendazole, fenbendazole, flubendazole, mebendazole, oxfendazole, oxibendazole and parbendazole.

In another embodiment, the Formula (I) compounds, Formula (II) compounds, aminoacetonitrile homologs, stereoisomers of said compound/homolog, or veterinarily acceptable salt of said compound/homolog thereof, are used in combination with an anthelmintic agent selected from tetramisole, levamisole, pyrantel pamoate, oxantel and morantel.

In another embodiment, the Formula (I) compounds, Formula (II) compounds, aminoacetonitrile homologs, stereoisomers of said compound/homolog, or veterinarily acceptable salt of said compound/homolog thereof, are used in combination with derivatives and analogues of the paraherquamide/marcfortine class of anthelmintic agents, particularly 2-desoxoparaherquamide.

In another embodiment of the invention, the Formula (I) compounds, Formula (II) compounds, aminoacetonitrile homologs, stereoisomers of said compound/homolog, or veterinarily acceptable salt of said compound/homolog thereof, are used in combination with a flukicide, for example a fasciolicide. Suitable agents include closantel, triclabendazole, clorsulon, rafoxanide, niclosamide, praziquantel and epsiprantel.

In another embodiment, the Formula (I) compounds, Formula (II) compounds, aminoacetonitrile homologs, stereoisomers of said compound/homolog, or veterinarily acceptable salt of said compound/homolog thereof, are used in combination with an ectoparasiticidal agent selected from fipronil, pyriprole, pyrafluprole, lufenuron, spiromesifen, tebufenozide, S-methoprene, hydroprene, pyriproxyfen, demiditraz, amitraz, tebufenozide, nitenpyram, spinosad, spinetoram, imidacloprid, dinotefuran, metaflumizone, flubendiamide, chlorantraniliprole, indoxacarb, pyridalyl, pyrimidifen and pyrifluquinazon.

In another aspect of the invention, the Formula (I) compounds, Formula (II) compounds, aminoacetonitrile homologs, stereoisomers of said compound/homolog, or veterinarily acceptable salt of said compound/homolog thereof, are used in a combination with at least two antiparasitic agents, as described herein. For example, the combination may include a) Formula (I) compounds, Formula (II) compounds, aminoacetonitrile homologs, stereoisomers of said compound/homolog, or veterinarily acceptable salt of said compound/homolog thereof, b) praziquantel, and c) moxidectin, and optionally d) S-methoprene. Similarly, the combination may include a) Formula (I) compounds, Formula (II) compounds, aminoacetonitrile homologs, stereoisomers of said compound/homolog, or veterinarily acceptable salt of said compound/homolog thereof, b) moxidectin or ivermectin or selamectin, c) fipronil or an isoxazoline, and optionally d) S-methoprene.

When the Formula (I) compounds, Formula (II) compounds, aminoacetonitrile homologs, stereoisomers of said compound/homolog, or veterinarily acceptable salt of said compound/homolog thereof, are used to treat a parasitic infection in a livestock animal then they may be used in combination with any of the agents commonly known in the art to be useful as feed additives for such livestock animals, and which are described in such manuals as "2006 Feed Additive Companion" and "Handbook of Feed Additives 2006". Suitable agents include:

polyether ionophores (such as lasalocid, monensin, salinomycin, narasin and laidlomycin);
  antibiotics (such as the tetracyclines, bacitracin, tylosin, tiamulin, lincomycin, virginiamycin, quinolone antibacterials and carbadox);
  steroid derivatives (such as melengesterol acetate);
  agents for the prevention or treatment of sub-acute rumen acidosis (such as sodium bicarbonate, acarbose and other amylase or glucosidase inhibitors);
  carcass quality/anabolic agents (such as beta adrenergic ligands, including ractopamine, salbutamol and almeterol); and
  other supplements (such as enzymes, minerals and vitamins).

The two components may be administered simultaneously, sequentially or separately. Where the two components are administered sequentially or separately then they may both be given by the same route, or they may be administered by different routes.

As used herein, simultaneous administration means the administration of both components to the host animal in a single action, which requires the two components to be incorporated into a single dosage unit, such as a single tablet or a single pour-on solution.

Sequential administration means the administration of each component is a separate action, but the two actions are linked. For example, administering a tablet comprising one component and a second tablet comprising the second component is considered to be sequential administration, even if the two tablets are given to the host animal at the same time.

Separate administration refers to the administration of each component independently of the other.

For convenience, simultaneous administration may be preferable. The two components may be presented in kit form. Such a kit comprises two or more separate pharmaceutical compositions, at least one of which contains a compound of formula (I) and one contains a further antiparasitic agent, and means for separately retaining said compositions, such as a container, divided bottle, or divided foil packet. An example of such a kit is the familiar blister pack used for the packaging of tablets, capsules and the like.

The kit is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

BIOLOGICAL ACTIVITY

Test compound was evaluated for activity against heartworm *Dirofilaria immitis* microfilariae in an in vitro microwell motility assay. Microfilaria were purified from microfilaremic canine blood by erythrocyte lysis and filtration and maintained in a cell culture media fortified with fetal bovine serum and antibiotics. The assay was conducted in a 384 well microtiter plate with 250 nL of DMSO solvated test compound and 25 µL of media containing approximately 200 microfilaria per well. The motility assessment was performed after 72 hours of incubation at 37° C. and 5% $CO_2$ on a LemnaTec Scanalyzer which determines motility of the microfilaria. The endpoint was defined as an $ED_{50}$ (dose at which the overall microfilaria motility was reduced by 50% compared to that of an untreated control). In this assay, test compounds 61-62, 64, 67, 71-72, and 78 had an $ED_{50}$ of 1 µM; test compounds 5, 27, 56, 60, 63, 65-66, 68-70, 75, 80-81, and 84 had an $ED_{50}$ of 3.3 µM; test compounds 1, 3-4, 14, 17, 20, 26, 31, 36, 39-40, 43, 51a, 53, 55, 57, 76-77, 79, 82-83, and 85-89 had an $ED_{50}$ of 10 µM; test compounds 6-8, 10-13, 16, 18, 22-25, 28-30, 32-33, 38, 41-42, 50, 54, 58, and 90 had an ED50 of 33 µM.

Some compounds were also tested against L4 stage larvae of *D. immitis*. The larvae were suspended in NCTC-135/IMDM medium in a 96-well plate and 1% test compound in DMSO. All compounds were screened at 10 µM concentration in duplicate. Motility was observed at 4, 24, 48 and 72 hours. The endpoint was defined as an $ED_{80}$ (dose at which 80% of larvae killed compared to that of an untreated control). Selamectin, moxidectin, ivermectin and milbemycin oxime were used as positive controls in this assay. In this assay, test compounds 1, 3-5, 7-8, 10-11, 13-14, 16, 18, 22-27, 29, 42-43, 51a, 60, 62-67, 69, and 80-81 were active against L4 *D. immitis* at 10 µM. The positive controls were all active against the L4 larvae at 10 µM.

The invention claimed is:
1. A method of treating a filarial endoparasitic infection in an animal in need thereof, comprising administering to said animal an effective amount of a Formula (I) compound

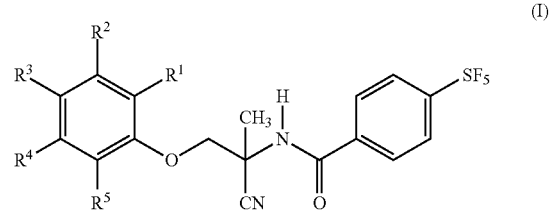

(I)

stereoisomer thereof, or a veterinarily acceptable salt thereof, wherein:
  $R^1$, $R^2$, $R^3$, $R^4$ and $R^5$ are each independently selected from U, halo, CN, $CF_3$, methyl, methoxy, —$OCF_3$, and —$SCH_3$, wherein said compound is effective in treating said endoparasitic infection.

2. The method of claim 1 wherein said Formula (1) compound is selected from the group consisting of:
  N-{1-cyano-2-{5-cyano-2-(trifluoromethyl)phenoxy}-1-methylethyl}-4-(pentafluorothio)benzamide;
  N-[2-(2-chloro-4-cyanophenoxy)-1-cyano-1-methylethyl]-4-(pentafluorothio)benzamide;
  N-{1-cyano-2-[5-cyano-2-(trifluoromethyl)phenoxy]-1-methylethyl}-4-(pentafluorothio)benzamide;
  N-[2-(2-chloro-5-cyanophenoxy)-cyano-1-methylethyl]-4-(pentafluorothio)benzamide;
  N-{1-cyano-2-[3-cyano-5-(trifluoromethyl)phenoxy]-1-methylethyl}-4-(pentafluorothio)benzamide;

N-[2-(3-chloro-4-cyanophenoxy)-1-cyano-1-methylethyl]-4-(pentafluorothio)benzamide;
N-{1-cyano-2-[4-cyano-2-(trifluoromethyl)phenoxy]-1-methylethyl}-4-(pentafluorothio)benzamide;
N-[1-cyano-2-(2,4-dichlorophenoxy)-1-methylethyl]-4-(pentafluorothio)benzamide;
N-[2-(3-chloro-5-cyanophenoxy)-1-cyano-1-methylethyl]-4-(pentafluorothio)-benzamide;
N-[2-(4-chlorophenoxy)-1-cyano-1-methylethyl]-4-(pentafluorothio)benzamide;
N-[2-(4-chloro-2-cyanophenoxy)-1-cyano-1-methylethyl]4(pentafluorothio)-benzamide;
N-[1-cyano-2-(2-cyanophenoxy)-1-methylethyl]-4-(pentafluorothio)benzamide;
N-[1-cyano-2-(4-iodophenoxy)-1-methylethyl]-4-(pentafluorothio)benzamide;
N-{1-cyano-1-methyl-2-[2-(trifluoromethyl)phenoxy]ethyl}-4-(pentafluorothio)-benzamide;
N-[1-cyano-2-(4-cyanophenoxy)-1-methylethyl]-4-(pentafluorothio)benzamide;
N-[2-(2-chlorophenoxy)-1-cyano-1-methylethyl]-4-(pentafluorothio)benzamide;
N-[2-(3-chloro-2-cyanophenoxy)-1-cyano-1-methylethyl]-4-(pentafluorothio)-benzamide;
N-[2-(2-chloro-4-fluorophenoxy)-1-cyano-1-methylethyl]-4-(pentafluorothio)-benzamide;
N-[1-cyano-2-(2-cyano-4-fluorophenoxy)-1-methylethyl]-4-(pentafluorothio)-benzamide;
N-[2-(4-chloro-2-fluorophenoxy)-1-cyano-1-methylethyl]-4-(pentafluorothio)-benzamide;
N-{2-[4-bromo-2-(trifluoromethyl)phenoxy]-1-cyano-1-methylethyl}-4-(pentafluorothio)benzamide;
N-{2-[2-chloro-4-(trifluoromethyl)phenoxy]-1-cyano-1-methylethyl}-4-(pentafluorothio)benzamide;
N-[2-(3-chloro-5-fluorophenoxy)-1-cyano-1-methylethyl]-4-(pentafluorothio)-benzamide;
N-[2-(3-chlorophenoxy)-1-cyano-1-methylethyl]-4-(pentafluorothio)benzamide;
N-[1-cyano-2-(3-cyano-5-fluorophenoxy)-1-methylethyl]-4-(pentafluorothio)-benzamide;
N-{1-cyano-2-[4-cyano-2-fluoro-6-(trifluoromethyl)phenoxy]-1-methylethyl}-4-(pentafluorothio)benzamide;
N-[2-(2-bromo-5-cyanophenoxy)-1-cyano-1-methylethyl]-4-(pentafluorothio)-benzamide;
N-[1-cyano-2-(3-cyanophenoxy)-1-methylethyl]-4-(pentafluorothio)benzamide;
N-[2-(2-bromo-4-cyanophenoxy)-1-cyano-1-methylethyl]-4-(pentafluorothio)-benzamide;
4-(2-cyano-2-{[4-(pentafluorothio)benzoyl]amino}propoxy)-3-(trifluoromethyl)-benzamide;
N-[2-(2-bromo-4-fluorophenoxy)-1-cyano-1-methylethyl]-4-(pentafluorothio)-benzamide;
N-[2-(4-bromo-2-fluorophenoxy)-1-cyano-1-methylethyl]-4-(pentafluorothio)-benzamide;
N-[2-(3-bromo-5-cyanophenoxy)-1-cyano-1-methylethyl]-4-(pentafluorothio)-benzamide;
N-[2-(2-chloro-3-fluorophenoxy)-1-cyano-1-methylethyl]-4-(pentafluorothio)-benzamide;
N-{1-no-2-[3-cyano-2-(trifluoromethyl)phenoxy]-1-methylethyl}-4-(pentafluorothio)-benzamide;
N-[2-(5-bromo-2-cyanophenoxy)-1-cyano-1-methylethyl]-4-(pentafluorothio)-benzamide;
N-[2-(2-bromo-3-cyanophenoxy)-1-cyano-1-methylethyl]-4-(pentafluorothio)-benzamide;
N-[1-cyano-2-(3,4-dichlorophenoxy)-1-methylethyl]-4-(pentafluorothio)benzamide;
N-[1-cyano-2-(2,5-dichlorophenoxy)-1-methylethyl]-4-(pentafluorothio)benzamide;
N-[1-cyano-2-(4-cyano-2-methylphenoxy)-1-methylethyl]-4-(pentafluorothio)-benzamide;
N-[1-cyano-2-(3-cyano-4-methoxyphenoxy)-1-methylethyl]-4-(pentafluorothio)-benzamide;
N-{1-cyano-2-[4-methoxy-2-trifluoromethyl)phenoxy]-1-methylethyl}-4-(pentafluorothio)benzamide;
N-[1-cyano-2-(5-cyano-2-methylphenoxy)-1-methylethyl]-4-(pentafluorothio)benzamide;
N-[1-cyano-2-(2,6-dichlorophenoxy)-1-methylethyl]-4-(pentafluorothio)benzamide;
N-[2-(2-chloro-6-fluorophenoxy)-1-cyano-1-methylethyl]-4-(pentafluorothio)-benzamide;
3-chloro-4-(2-cyano-2-{[4-(pentafluorothio)benzoyl]amino}propoxy)benzamide;
4-cyano-2-(2-cyano-2-{[4-(pentafluorothio)benzoyl]amino}propoxy)benzamide;
3-cyano-5-(2-cyano-2-{[4-(pentafluorothio)benzoyl]amino}propoxy)benzamide;
N-[1-cyano-2-(2,4-dicyanophenoxy)-1-methylethyl]-4-(pentafluorothio)benzamide;
N-{2-[3-chloro-2-(trifluoromethyl)phenoxy]-1-cyano-1-methylethyl}-4-(pentafluorothio)benzamide;
N-{1-cyano-2-[4-cyano-2-(trifluoromethyl)phenoxy]-1-methylethyl}-4-(pentafluorothio)benzamide;
N-{(1S)1-cyano-2-[4-cyano-2-(trifluoromethyl)phenoxy]-1-methylethyl}-4-pentafluorothio)benzamide;
N-[1-cyano-2-(4-cyano-2,6-difluorophenoxy)-1-methylethyl]-4-(pentafluorothio)-benzamide;
N-(1-cyano-1-methyl-2-{[4-(methylthio)benzyl]oxy}ethyl)-4-(pentafluorothio)-benzamide;
N-[1-cyano-2-(2-cyano-4,6-difluorophenoxy)-1-methylethyl]-4-(pentafluorothio)-benzamide;
N-{1-cyano-2-[5-cyano-2-(trifluoromethoxy)phenoxy]-1-methylethyl}-4-(pentafluorothio)benzamide;
N-{1-cyano-2-[4-cyano-2-(trifluoromethoxy)phenoxy]-1-methylethyl}-4-(pentafluorothio)benzamide;
N-[2-(2-chloro-5-cyanophenoxy)-1-cyano-1-methylethyl]-4-(pentafluorothio)-benzamide;
N-[2-(2-bromo-4,5-difluorophenoxy)-1-cyano-1-methylethyl]-4-(pentafluorothio)benzamide; and
N-{1-cyano-2-[4,5-difluoro-2-(trifluoromethyl)phenoxy]-1-methylethyl}-4-(pentafluorothio)benzamide, stereoisomer thereof, or a veterinarily acceptable salt of said compound or stereoisomer thereof.

3. The method of claim 2 wherein said Formula (1) compound is selected from the group consisting of:
N-{1-cyano-2-[3-cyano-5-(trifluoromethyl)phenoxy]-1-methylethyl}-4-(pentafluorothio)benzamide;
N-[2-(2-bromo-5-cyanophenoxy)-1-cyano-1-methylethyl]-4-(pentafluorothio)-benzamide; and
N-{(1S)1-cyano-2-[4-cyano-2-(trifluoromethyl)phenoxy]-1-methylethyl}-4-pentafluorothio)benzamide, stereoisomer thereof, or a veterinarily acceptable salt of said compound or stereoisomer thereof, and wherein said animal is a companion animal.

4. A method of treating a filarial endoparasitic infection in an animal in need thereof, comprising administering to said animal an effective amount of a Formula (II) compound

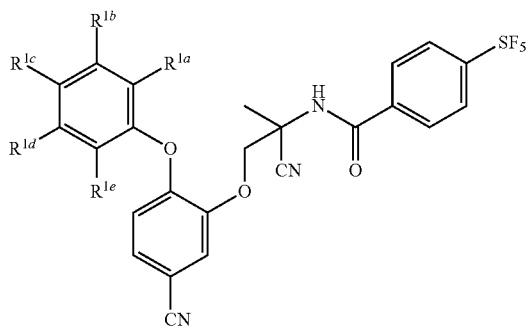

(II)

stereoisomer thereof; or a veterinarily acceptable salt thereof; wherein;

wherein $R^{1a}$, $R^{1b}$, $R^{1d}$, and $R^{1e}$ are each independently selected from the group consisting of hydrogen, halo, $CF_3$, —$OCH_3$, methyl, and hydroxyl.

5. The method of claim 4 wherein said Formula (11) compound is selected from the group consisting of:
N-[1-cyano-2-(5-cyano-2-phenoxyphenoxy)-1-methylethyl]-4-(pentafluorothio)benzamide;
N-{1-cyano-2-[5-cyano-2-(4-fluorophenoxy)phenoxy]-1-methylethyl}-4-(pentafluorothio)benzamide;
N-{2-[2-(4-chloro-2-fluorophenoxy)-5-cyanophenoxy]-1-cyano-1-methylethyl}-4-(pentafluorothio)benzamide;
N-{2-[2-(2-chloro-4-fluorophenoxy)-5-cyanophenoxy]-1-cyano-1-methylethyl}-4-(pentafluorothio)benzamide;
N-{2-[2-(4-chlorophenoxy)-5-cyanophenoxy]-1-cyano-1-methylethyl}-4-(pentafluorothio)benzamide;
N-{1-cyano-2-[5-cyano-2-(2,4-dichlorophenoxy)phenoxy]-1-methylethyl}-4-(pentafluorothio)benzamide;
N-(1-cyano-2-[5-cyano-2-(4-methoxyphenoxy)phenoxy]-1-methylethyl)-4-(pentafluorothio)benzamide;
N-(1-cyano-2-{5-cyano-2-[4-(trifluoromethyl)phenoxy]phenoxy}-1-methylethyl)-4-(pentafluorothio)benzamide;
N-{1-cyano-2-[5-cyano-2-(3-methoxyphenoxy)phenoxy]-1-methylethyl}-4-(pentafluorothio)benzamide;
N-{1-cyano-2-[5-cyano-2-(2-methoxyphenoxy)phenoxy]-1-methylethyl}-4-(pentafluorothio)benzamide;
N-{1-cyano-2-[5-cyano-2-(4-fluoro-2-methylphenoxy)phenoxy]-1-methylethyl}-4-(pentafluorothio)benzamide;
N-{2-[2-(2-chloro-4-methylphenoxy)-5-cyanophenoxy]-1-cyano-1-methylethyl}-4-(pentafluorothio)benzamide;
N-{1-cyano-2-[5-cyano-2-(2,4-dimethylphenoxy)phenoxy]-1-methylethyl}-4-(pentafluorothio)benzamide;
N-{1-cyano-2-[5-cyano-2-(2-fluorophenoxy)phenoxy]-1-methylethyl}-4-(pentafluorothio)benzamide;
N-{1-cyano-2-[5-cyano-2-(2-fluoro-4-methoxyphenoxy)phenoxy]-1-methylethyl}-4-(pentafluorothio)benzamide;
N-{2-[2-(2-chloro-4-methoxyphenoxy)-5-cyanophenoxy]-1-cyano-1-methylethyl}-4-(pentafluorothio)benzamide;
N-{1-cyano-2-[5-cyano-2-(2,3-difluoro-4-methoxyphenoxy)phenoxy]-1-methylethyl}-4-(pentafluorothio)benzamide;
N-{1-cyano-2-[5-cyano-2-(2,6-difluoro-4-methoxyphenoxy)phenoxy]-1-methylethyl}-4-(pentafluorothio)benzamide;
N-{1-cyano-2-[5-cyano-2-(3,5-difluoro-4-methoxyphenoxy)phenoxy]-1-methylethyl}-4-(pentafluorothio)benzamide; and
N-{1-cyano-2-[5-cyano-2-(4-hydroxy-2-methoxyphenoxy)phenoxy]-1-methylethyl}-4-(pentafluorothio)benzamide, stereoisomer thereof, or a veterinarily acceptable salt thereof, wherein said compound is effective in treating said endoparasitic infection.

6. The method of claim 5 wherein said Formula (II) compound is selected from the group consisting of:
N-{1-cyano-2-[5-cyano-2-(4-fluorophenoxy)phenoxy]-1-methylethyl}-4-(pentafluorothio)benzamide;
N-{2-[2-(4-chloro-2-fluorophenoxy)-5-cyanophenoxy]-1-cyano-1-methylethyl}-4-(pentafluorothio)benzamide;
N-{2-[2-(4-chlorophenoxy)-5-cyanophenoxy]-1-cyano-1-methylethyl}-4-(pentafluorothio)benzamide;
N-(1-cyano-2-{5-cyano-2-[4-(trifluoromethyl)phenoxy]phenoxy}-1-methylethyl)-4-(pentafluorothio)benzamide;
N-{2-[2-(2-chloro-4-methylphenoxy)-5-cyanophenoxy]-1-cyano-1-methylethyl}-4-(pentafluorothio)benzamide;
N-{1-cyano-2-[5-cyano-2-(2,4-dimethylphenoxy)phenoxy]-1-methylethyl}-4-(pentafluorothio)benzamide; and
N-{1-cyano-2-[5-cyano-2-(3,5-difluoro-4-methoxyphenoxy)phenoxy]-1-methylethyl}-4-(pentafluorothio)benzamide, stereoisomer thereof, or a veterinarily acceptable salt thereof, wherein said compound is effective in treating said endoparasitic infection and wherein said animal is a companion animal.

7. The method according to claim 1, or 4, wherein said filarial endoparasitic infection is caused by an endoparasite selected from *Brugia malayi, Brugia pahangi, Brugia timori, Wuchereria bancrofti, Dirofilaria immitis, Dirofilaria repens, Dirofilaria ursi, Dirofilaria tenuis, Dirofilaria spectans, Dirofilaria lutrae, Dipetalonema reconditum, Dipetalonema repens, Onchocerca gibsoni, Onchocerca gutturosa*, and *Onchocerca volvulus*, or combinations thereof.

8. The method of claim 7 wherein the filarial endoparasitic infection is caused by *Dirofilarial* endoparasites.

9. The method of claim 8, wherein the *Dirofilarial* endoparasite is *Dirofilaria immitis*.

10. The method of claim 9 further comprising at least one additional veterinary agent, selected from the group consisting of ivermectin, avermectin, abamectin, emamectin, eprinomectin, doramectin, selamectin, moxidectin, nemadectin, milbemycin oxime, albendazole, demiditraz, amitraz, oxfendazole, levamisole, pyrantel pamoate, praziquantel, 2-desoxoparaherquamide, fipronil, spinosad, imidacloprid, indoxacarb, S-methoprene, pyriproxyfen, and an isoxazoline selected from the group consisting of 5-(3,5-dichloro-4-fluorophenyl)-3-(4-{3-fluoro-1-[(methylsulfonyl)acetyl]azetidin-3-yl}phenyl)-5-(trifluoromethyl)-4,5-dihydroisoxazole; 1-(3-fluoro-3-(4-(5-(3,4,5-trichlorophenyl)-5-(trifluoromethyl)-4,5-dihydroisoxaz-3-yl)phenyl)azetidin-1-yl)-2-(methylsulfonyl)ethanone; 1-(3-(4-(5-(3,5-dichlorophenyl)-5-(trifluoromethyl)-4,5-dihydroisoxazol-3-yl)phenyl)-3-fluoroazetidin-1-yl)-2-(methylsulfonyl)ethanone; (3-(4-(5-(3,5-dichloro-4-fluorophenyl)-5-(trifluoromethyl)-4,5-dihydroisoxazol-3-yl)phenyl)-3-fluoroazetidin-1-yl)(1,1-dioxidothietan-3-yl)methanone; (1,1-dioxidothietan-3-yl)(3-fluoro-3-(4-(5-(3,4,5-trichlorophenyl)-5-

(trifluoromethyl)-4,5-dihydroisoxazol-3-yl)phenyl)azetidin-1-yl)methanone; (3-(4-(5-(3,5-dichlorophenyl)-5-(trifluoromethyl)-4,5-dihydroisoxazol-3-yl)phenyl)-3-fluoroazetidin-1-yl)(1,1-dioxidothietan-3-yl)methanone; 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 2-(methylsulfonyl)-1-(5'-(5-(3,4,5-trichlorophenyl)-5-(trifluoromethyl)-4,5-dihydroisoxazol-3-yl)-3'H-spiro[azetidine-3,1'-isobenzofuran]-1-yl)ethanone; 1-(5'-(5-(3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; 4-(5-(3,5-dichlorophenyl)-5-(trifluoromethyl)-4,5-dihydroisoxazol-3-yl)-N-(2-oxo-2-((2,2,2-trifluoroethyl)amino)ethyl)-1-naphthamide; 4-(5-(3,5-dichlorophenyl)-5-(trifluoromethyl)-4,5-dihydroisoxazol-3-yl)-2-methyl-N-(2-oxo-2-((2,2,2-trifluoroethyl)amino)ethyl)benzamide; (S)-2-((4-(5-(3,5-dichlorophenyl)-5-(trifluoromethyl)-4,5-dihydroisoxazol-3-yl)-2-methylphenyl)sulfonyl)-N-(2,2,2-trifluoroethyl)acetamide; 4-(5-(3,5-dichloro-4-fluorophenyl)-5-(trifluoromethyl)-4,5-dihydroisoxazol-3-yl)-N-(1,1-dioxidothietan-3-yl)-2-methylbenzamide; 4-(5-(3,5-dichlorophenyl)-5-(trifluoromethyl)-4,5-dihydrofuran-3-yl)-N-(1,1-dioxidothietan-3-yl)-2-methylbenzamide; and 4-(5-(3,5-dichlorophenyl)-5-(trifluoromethyl)-4,5-dihydroisoxazol-3-yl)-N-(1,1-dioxidothietan-3-yl)-1-naphthamide; and 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, or combinations thereof.

11. The method of claim 10, wherein the additional veterinary agent is selected from moxidectin, milbemycin oxime, ivermectin, selamectin, 1-(5'-(5-(3,5-dichloro-4-fluorophenyl)-5-(trifluoromethyl)-4,5-dihydroisoxazol-3-yl)-3'H-spiro[azetidine-3,1'-isobenzofuan]-1-yl)-2-(methylsulfonyl)ethanone; or mixture thereof.

12. A compound selected from the group consisting of
- N-{1-cyano-2-[5-cyano-2-(4-fluorophenoxy)phenoxy]-1-methylethyl}-4-(pentafluorothio)benzamide;
- N-{2-[2-(4-chloro-2-fluorophenoxy)-5-cyanophenoxy]-1-cyano-1-methylethyl}-4-(pentafluorothio)benzamide;
- N-{2-[2-(4-chlorophenoxy)-5-cyanophenoxy]-1-cyano-1-methylethyl}-4-(pentafluorothio)benzamide;
- N-(1-cyano-2-{5-cyano-2-[4-(trifluoromethyl)phenoxy]phenoxy}-1-methylethyl)-4-(pentafluorothio)benzamide;
- N-{2-[2-(2-chloro-4-methylphenoxy)-5-cyanophenoxy]-1-cyano-1-methylethyl}-4-(pentafluorothio)benzamide;
- N-{1-cyano-2-[5-cyano-2-(2,4-dimethylphenoxy)phenoxy]-1-methylethyl}-4-(pentafluorothio)benzamide; and
- N-{1-cyano-2-[5-cyano-2-(3,5-difluoro-4-methoxyphenoxy)phenoxy]-1-methylethyl}-4-(pentafluorothio)benzamide, stereoisomers, and pharmaceutically or veterinarily acceptable salts thereof.

13. The method of claim 3 or 6 wherein the companion animal is a dog.

* * * * *

UNITED STATES PATENT AND TRADEMARK OFFICE
CERTIFICATE OF CORRECTION

PATENT NO.       : 8,962,681 B2
APPLICATION NO.  : 14/351945
DATED            : February 24, 2015
INVENTOR(S)      : Conder et al.

It is certified that error appears in the above-identified patent and that said Letters Patent is hereby corrected as shown below:

In the claims

Column 18, line 64, should read:
"N-[2-(2-chloro-5-cyanophenoxy)-1-cyano-1-methylethyl]-"

Column 19, line 12, should read:
"ethyl]-4-(pentafluorothio)-benzamide;"

Column 19, line 60, should read:
"N-{1-cyano-2-[3-cyano-2-(trifluoromethyl)phenoxy]-1-me-"

Column 20, line 61, should read:
"noxy]-1-methylethyl}-4-pentafluorothiobenzamide,"

Signed and Sealed this
Third Day of November, 2015

Michelle K. Lee
*Director of the United States Patent and Trademark Office*